United States Patent [19]
Tröger et al.

[11] 3,983,131
[45] Sept. 28, 1976

[54] PROCESS FOR THE PRODUCTION OF 1,1'-PEROXYDICYCLOHEXYLAMINE
[75] Inventors: Jürgen Tröger, Grossauheim; Otto Weiberg, Neu-Isenburg; Wolfgang Weigert, Offenbach (Main), all of Germany
[73] Assignee: Deutsche Gold- und Silber-Scheideanstalt vormals Roessler, Germany
[22] Filed: Jan. 20, 1971
[21] Appl. No.: 108,195

[30] Foreign Application Priority Data
Jan. 26, 1970 Germany............................ 2003269
Jan. 31, 1970 Germany............................ 2004440

[52] U.S. Cl. ........................................ 260/307 FB
[51] Int. Cl.² ..................................... C07D 273/00
[58] Field of Search................................ 260/307 F

[56] References Cited
UNITED STATES PATENTS
3,707,444  12/1972  Schreyer et al. ..................... 203/51
FOREIGN PATENTS OR APPLICATIONS
1,531,062  5/1968  France Primary Examiner—Raymond V. Rush
Attorney, Agent, or Firm—Cushman, Darby & Cushman

[57] ABSTRACT
1,1'-peroxydicyclohexylamine is prepared from cyclohexanone, hydrogen peroxide and ammonia in the absence of catalyst and under anhydrous form. The ammonia is in gaseous or liquid form.

5 Claims, No Drawings

PROCESS FOR THE PRODUCTION OF 1,1'-PEROXYDICYCLOHEXYLAMINE

According to Dutch application 6,817,827, it is known to carry out the production of caprolactam by splitting 1,1'-peroxydicyclohexylamine. This 1,1'-peroxydicyclohexylamine having the formula

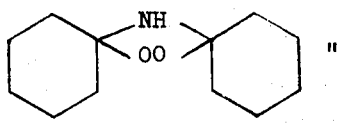

can be obtained according to Dutch application 6,817,827, from aqueous hydrogen peroxide solutions, or an organic oxidation mixture of isopropanol and atmospheric oxygen, together with cyclohexanone and aqueous ammonia to which additional gaseous ammonia can be added. The reaction is carried out in the presence of organic catalysts and stabilizers.

The reaction takes place with cooling initially at temperatures as low as 0° C. and then is completed at higher temperatures. The yield of crude product is about 70% based on the hydrogen peroxide or cyclohexanone.

However, the industrial carrying out of this known process is very difficult. Thus, besides the water formed in the reaction, there is present in the reaction mixture considerable additional amounts of water which are introduced by the aqueous hydrogen peroxide and ammonia solution. The use of the oxidation mixture of isopropanol is uninteresting since, besides the cyclohexanone, other organic materials are thereby introduced which have nothing to do with the reaction, such as unreacted isopropanol and acetone. The reaction product in each case must be isolated as such and only then can be put to further use. Because of considerable amounts of water or foreign organic materials, each superfluous charge requires separate steps for separation of this ballast. Acetone itself causes the formation of byproducts.

Thus in the above identified Dutch application the reaction mixture is extracted with petroleum ether in which the reaction product as well as cyclohexanone and the stabilizers dissolve. After distilling off the ether and cyclohexanone the crude product is recovered from this extract. Petroleum ether and cyclohexanone must be worked up separately.

On the other hand it has now been found that the carrying out of the process for the production of 1,1'-peroxydicyclohexylamine can be substantially simplified and the yield of this end product greatly increased if hydrogen peroxide is reacted with gaseous or liquid, preferably anhydrous, ammonia without use of a catalyst and if the hydrogen peroxide is employed in a water free, i.e. anhydrous, solution of cyclohexanone. Such a solution of hydrogen peroxide in cyclohexanone can be, for example, the solution recovered in Schreyer U.S. application Ser. No. 79,315 filed Oct. 8, 1970, now U.S. Pat. No. 3,707,444 (corresponding to German application P 19 51 211.9). In a given case a known stabilizer can be present.

The solution of hydrogen peroxide in cyclohexanone can be of any concentration, par example 1 to 20 weight % x, preferably 10 to 20 weight % x solutions are employed.

The ammonia is added to this solution, either as gaseous ammonia or as liquid ammonia in an autoclave. In the first case the ammonia is introduced into the solution till the end of the reaction, see example 1. It is more economical to choose the molar quantity or a slight molar excess of ammonia in relation to the applied hydrogen peroxide. On principle the excess can increase up to double or triple the molar quantity.

As the reaction temperature, room temperature can be employed. However, higher temperatures can also be employed, preferably up to 80° C. Temperatures lower than room temperature are not necessary. While temperature is not a critical feature of the invention, the temperature can range for example from 0°C to 80° C. Thus there can be used a temperature of 20° to 80°C.

The process of the invention can be carried out batchwise, for example in stirrer reactors, or continuously, for example in flow through reactors.

The reaction partners hydrogen peroxide in cyclohexanone and ammonia are brought to reaction in a reactor at the indicated temperature, preferably in presence of a conventional stabilizer. The reaction mixture of 1,1'-peroxydicyclohexylamine, unreacted cyclohexanone, water of reaction and in a given case some ammonia (which can be removed by a short passing through of an inert gas such as nitrogen) is thus as such, immediately available for production of caprolactam. The small amounts of water of reaction distills off immediately under the condition of caprolactam production.

In other words, the reaction of cyclohexanone, hydrogen peroxide and ammonia for the production of 1,1'-peroxydicyclohexylamine is so conducted according to the process of the invention that the reaction mixture for the production of caprolactam can be used immediately.

If, however, the end product is to be recovered as a water free solution or in crystalline form then, after the passage of an inert gas to free the mixture of ammonia, the reaction mixture is in a second step, first heated to the boiling point of the azeotrope of water and cyclohexanone and the water of reaction removed in this way. After condensation and phase separation of the azeotrope the cyclohexanone is returned to the starting step. 1,1'-peroxydicyclohexylamine now is present as a water free solution in cyclohexanone. If it is to be produced as a crystalline product the cyclohexanone is distilled off by increasing the temperature.

As a theoretical possibility it has also been suggested to add 100% hydrogen peroxide for the reaction for the production of 1,1'-peroxydicyclohexylamine. Such a reaction, of course, can in practice, not be carried out since there is a very great danger of explosion.

The technical advantage of the process is that after a single step a reaction mixture occurs which can be used immediately for the production of caprolactam. The introduction of larger amounts of water which require the employment of extraction agents foreign to the reaction in the further course of the process or the carrying along of organic material foreign to the reaction, is eliminated. Additionally in the latter case, the oxidation mixtures of foreign organic materials must first be prepared by circumstantial procedures.

If the reaction product is to be isolated according to the process of the invention a simple distillation of first the water and next the cyclohexanone suffices.

Furthermore, the yields of end product are at least 80%, generally even higher, based on the hydrogen peroxide added.

The following examples further illustrate the invention.

Unless otherwise indicated all parts and percentages are by weight.

EXAMPLE 1

100 grams of cyclohexanone were placed in a reactor and ammonia gas introduced up to saturation at 60° C. This took about 5 minutes. Within 30 minutes 100 grams of a solution of 18 weight % hydrogen peroxide in cyclohexanone was added dropwise, which contained 50 mg. of hydroxyethane diphosphonic acid as a stabilizer. The temperature was held at 60° C. and gaseous ammonia was introduced during 2 hours. The resulting reaction mixture contained 85 weight % of 1,1'-peroxydicyclohexylamine based on the hydrogen peroxide added (proved by production of 1,1'-peroxydicyclohexylamine sulfate), and could be converted immediately to caprolactam in known manner after expelling the residual ammonia.

If desired the water of reaction can be distilled off by distillation of the azeotrope of water and cyclohexanone in a slight vacuum, e.g. 100 to 50 Torr. After condensation the components of the azeotrope formed two layers.

1,1'-peroxydicyclohexylamine can be recovered in pure form by distilling off the cyclohexanone in vacuum, e.g. from 30 to 1 Torr, and finally recrystallization in alcohol-water. The yield corresponds to that mentioned above.

EXAMPLE 2

In a pickled steel autoclave a water free solution of 12.3 grams of hydrogen peroxide and 0.1 grams of hydroxyethane diphosphonic acid were heated at 60°C. in 193.7 grams of cyclohexanone. Within 5 minutes 6.51 grams of liquid ammonia were metered in with stirring from a steel bomb attached to the autoclave. This corresponds to an excess of 5.9% $NH_3$ based on the hydrogen peroxide added. The mixture was stirred an additional hour at 60° C. The reaction product was concentrated on a rotatory evaporator at 40° C. and 1.5 Torr. After distilling off most of the cyclohexanone, 20 ml. of water were mixed in with the sump to facilitate the distillation of the residual cyclohexanone (as a water-cyclohexanone azeotrope). 73.5 grams of crude 1,1'-peroxydicyclohexylamine (M. P. 33° —36° C.) with a peroxygen content of 15.6% (Theory peroxygen content 16.11%) remained behind, The yield of 1,1'-peroxydicyclohexylamine (based on the hydrogen peroxide added) amounted to 93% of theory.

What is claimed is:

1. In a process for the production of 1,1'-peroxydicyclohexylamine having the formula

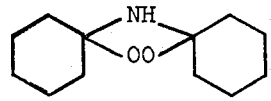

by reacting cyclohexanone, hydrogen peroxide and ammonia, the improvement consisting essentially of carrying out the reaction in the absence of catalyst with a 1 to 20 weight % solution of hydrogen peroxide in cyclohexanone and ammonia as gaseous or liquid ammonia, the only water present during the reaction being that formed in the reaction at a temperature of 20° to 80°C.

2. A process according to claim 1 wherein the water formed in the reaction is removed by azeotropic distillation with unreacted cyclohexanone after the product is formed.

3. A process according to claim 1 wherein the hydrogen peroxide is added as a 10 to 20 weight % solution in cyclohexanone.

4. A process according to claim 1 wherein the ammonia is added as gaseous ammonia.

5. A process according to claim 1 wherein the ammonia is added as liquid ammonia.

* * * * *